United States Patent
Cader et al.

(10) Patent No.: US 10,444,147 B2
(45) Date of Patent: Oct. 15, 2019

(54) OPTICAL BIOFILM PROBE

(71) Applicant: Hewlett Packard Enterprise Development LP, Houston, TX (US)

(72) Inventors: Tahir Cader, Liberty Lake, WA (US); John Franz, Houston, TX (US); William K Norton, Houston, TX (US)

(73) Assignee: HEWLETT PACKARD ENTERPRISE DEVELOPMENT LP, Houston, TX (US)

( * ) Notice: Subject to any disclaimer, the term of this patent is extended or adjusted under 35 U.S.C. 154(b) by 642 days.

(21) Appl. No.: 15/211,875

(22) Filed: Jul. 15, 2016

(65) Prior Publication Data

US 2018/0017490 A1    Jan. 18, 2018

(51) Int. Cl.
| | |
|---|---|
| *G01N 21/00* | (2006.01) |
| *G01N 21/59* | (2006.01) |
| *G01N 21/85* | (2006.01) |
| *G01N 21/94* | (2006.01) |
| *G01N 21/47* | (2006.01) |

(52) U.S. Cl.
CPC .............. *G01N 21/59* (2013.01); *G01N 21/85* (2013.01); *G01N 21/94* (2013.01); *G01N 21/4738* (2013.01); *G01N 2201/12* (2013.01)

(58) Field of Classification Search
CPC .... G01N 21/4738; G01N 21/59; G01N 21/85; G01N 21/94; G01N 15/1463; G01N 33/1893; G01N 2015/0088; G01N 2201/12; G01N 2201/129
USPC ................................ 356/432–444; 435/288.7
See application file for complete search history.

(56) References Cited

U.S. PATENT DOCUMENTS

| | | | |
|---|---|---|---|
| 6,800,478 B2 | 10/2004 | Castellini | |
| 9,763,364 B1* | 9/2017 | Amoah-Kusi | F28F 13/08 |
| 2006/0254343 A1 | 11/2006 | Saxena et al. | |
| 2015/0247790 A1* | 9/2015 | Okumus | G01N 15/1459 |
| | | | 506/12 |

FOREIGN PATENT DOCUMENTS

WO    WO-2007093374 A1    8/2007

OTHER PUBLICATIONS

Shira L. Broschat, et al., "Optical reflectance assay for the detection of biofilm formation", Journal of Biomedical Optics, Jul. 22, 2005, Journal of Biomedical Optics, 6 pages, vol. 10(4).

* cited by examiner

*Primary Examiner* — Sunghee Y Gray
(74) *Attorney, Agent, or Firm* — Hewlett Packard Enterprise Patent Department

(57) ABSTRACT

Example implementations relate to an optical biofilm probe. For example, in an implementation, the optical biofilm probe may include a light source to project light towards a substrate disposed within a bypass and a detector to detect light from the substrate. Properties of light detected by the detector may be affected by biofilm formation on the substrate. The bypass may be connected in parallel to a conduit of a fluid system.

9 Claims, 6 Drawing Sheets

OPTICAL BIOFILM PROBE

BACKGROUND

Fluid systems, such as liquid-cooling systems, may move fluid within conduits. Contamination in the fluid may lead to the formation of a biofilm. Biofilm may cause corrosion and deterioration.

BRIEF DESCRIPTION OF THE DRAWINGS

Various examples will be described below with reference to the following figures.

DETAILED DESCRIPTION

Figure 1:
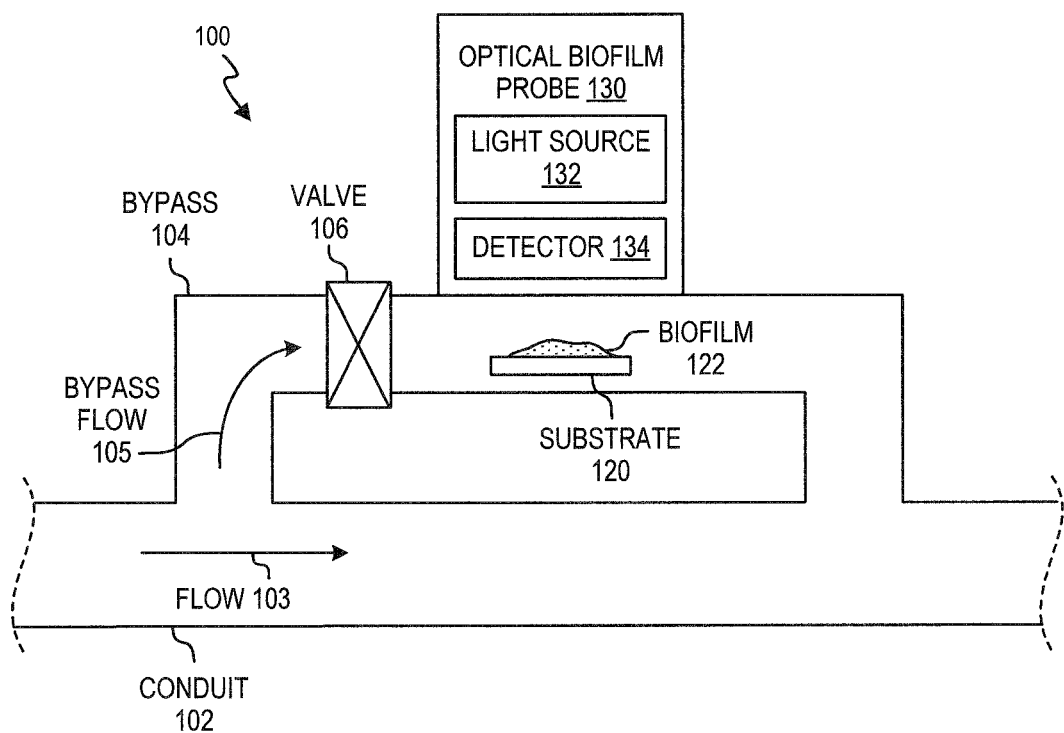
FIG. 1 depicts a diagram of an example apparatus that includes an optical biofilm probe at a bypass.

Fluid systems move fluid within conduits in a recirculating or non-recirculating manner. Among other applications, fluid systems may be employed as a heat transfer element, and may be useful for heating, cooling, or thermal regulation. For example, some computing systems, including high performance computing systems, may employ a fluid system (more particularly, also referred to as a liquid-cooling system) that circulates coolant through conduits and over heat transfer surfaces adjacent to heat-generating components, such as processors, memory, or storage. Heat from the components is transferred away by the coolant.

However, contamination in the fluid of fluid systems can result in microbial growth on wetted heat transfer surfaces, as well as corrosion or other deteriorative effects. Microbial growth on heat transfer surfaces can cause corrosion and deterioration and reduced heat transfer efficiency, which can lead to overheating and damage of the larger system (e.g., a computing system). Microbial growth may start with a few cells depositing on a surface, which may increase into fully formed biofilms—a population of microbial organisms in a matrix of organic materials produced by the microbial organisms themselves. Once formed, biofilms may be hardy and difficult to remove from a fluid system, sometimes requiring costly decontamination procedures or part replacement.

To reduce incidences of microbial growth, anti-microbial chemicals or biocides may be added to the fluid, and the fluid may be monitored regularly to verify that an appropriate chemistry is maintained. The process of monitoring may include manually extracting a sample of the fluid, followed by on-site testing or sending the sample to an external lab for testing. Lab testing may include subjecting the fluid sample to a culture test in a Petri dish or testing the composition of the fluid. Some testing may be expensive or difficult to perform. After receiving results of the lab testing, appropriate chemicals may then be added to re-balance the fluid system. However, a considerable amount of time may elapse between initial fluid sampling and receipt of test results, and a contamination or biofilm problem may worsen in the meantime. Accordingly, monitoring the fluid in this way may be a cumbersome, expensive, intrusive, and sometimes untimely means of preventing microbial growth in fluid systems.

Examples disclosed herein may relate to, among other things, an optical biofilm probe at a bypass connected in parallel to a conduit of a fluid system. The bypass may be isolated from fluid flow in the fluid system, for measurements by the optical biofilm probe. The optical biofilm probe may include a light source to project light towards a substrate disposed within the bypass and a detector to detect light from the substrate. Properties of light detected by the detector may be affected by biofilm formation on the substrate. By virtue of such an optical biofilm probe, biofilm incipience and formation in the fluid system may be detected and monitored in real time, thus enabling timely intervention and corrective action.

Referring now to the figures, FIG. 1 depicts a diagram of an example apparatus 100 for monitoring for the development of a biofilm in a fluid system. In some implementations, the fluid system may serve as a liquid-cooling system of a computing system (e.g., a server, a high performance computing system, a storage system, etc.). The apparatus 100 may be employed in other types of fluid systems as well, where fluid purity and low contamination levels are desirable, such as potable water distribution systems, or fluid delivery systems in industrial, manufacturing medical, or dental settings, or the like. The fluid system may include a conduit 102 in which a fluid, such as water or a coolant, may flow (flow 103).

The apparatus 100 includes a bypass 104 that is connected in parallel to the conduit 102 of the fluid system. In some implementations, the bypass 104 may recirculate back into the conduit 102, and in other implementations, the bypass 104 may lead to a waste line rather than recirculating back into the conduit 102.

The apparatus 100 includes a valve 106 that can isolate the bypass 104 from the fluid flow 103 of the fluid system. For example, with the valve 106 in an open position, fluid may branch off of the conduit 102 into the bypass 104 as flow 105. With the valve 106 in a closed position, flow 105 is blocked, and fluid downstream of the valve 106 may be rendered substantially still or quiescent, or at least more still or quiescent compared to flow 105. Fluid quiescence in the bypass 104 may be useful for reducing aberrations or artifacts in measurements performed by the optical biofilm probe 130. For example, fluid velocity, velocity gradients, turbulent eddies, and other flow properties and patterns in flow 105 may affect the light measurement of the optical biofilm probe 130 described below.

A substrate 120 may be disposed within the bypass 104. The substrate 120 may be in contact with fluid of the fluid system. For example, when the valve 106 is opened, flow 105 through the bypass 104 will flow over the substrate. Contamination in the fluid, such as microbial organisms or other biological contamination, may deposit onto the substrate 120 and develop over time into a biofilm 122. The substrate 120 may be formed from a material conducive to or at least noninhibitive of biofilm deposition and formation. In some implementations, the substrate 120 may be glass or a polymeric material, such as polystyrene or the like. The substrate 120 may be in the shape of a flat plate in some implementations.

The apparatus 100 includes an optical biofilm probe 130 at the bypass 104 to detect biofilm formation on the substrate 120. In particular, the optical biofilm probe 130 may include a light source 132 and a detector 134. The light source 132 may project light into the bypass 104 and at (e.g., towards) the substrate 120. The detector 134 may detect light from the substrate 120. In some implementations, the detector 134 may be tuned or selected to detect the particular wavelengths emitted by the light source 132. Properties of light detected by the detector 134, such as intensity, may be a function of or may be affected by biofilm formation on the substrate 120, as will described further with respect to FIGS. 2 and 3.

In some implementations, the light source 132 may emit light over a spectrum of wavelengths including the near-infrared region, visible region, and/or ultraviolet region. In some implementations, the light source 132 may emit light primarily in the near-infrared and/or visible region, to reduce or avoid any inhibition of biofilm growth due to any antimicrobial effect of ultraviolet light. In some implementations, the light source 132 may emit light of particular wavelength(s) (e.g., visible spectrum) to promote and accelerate growth of biofilm, which may increase the detection sensitivity of the apparatus 100 to biofilm formation.

In some implementations, the light source 132 (or a separate light source not shown) may emit ultraviolet light to terminate biofilm growth on the substrate 120. Termination of biofilm growth may affect properties of light detected by the detector 134 in a manner that is, for example, an inverse of the effect of positive biofilm growth on light detected by the detector 134. Thus, attempting to terminate biofilm growth using ultraviolet light may be useful for validating readings by the optical biofilm probe 130.

Figure 2:
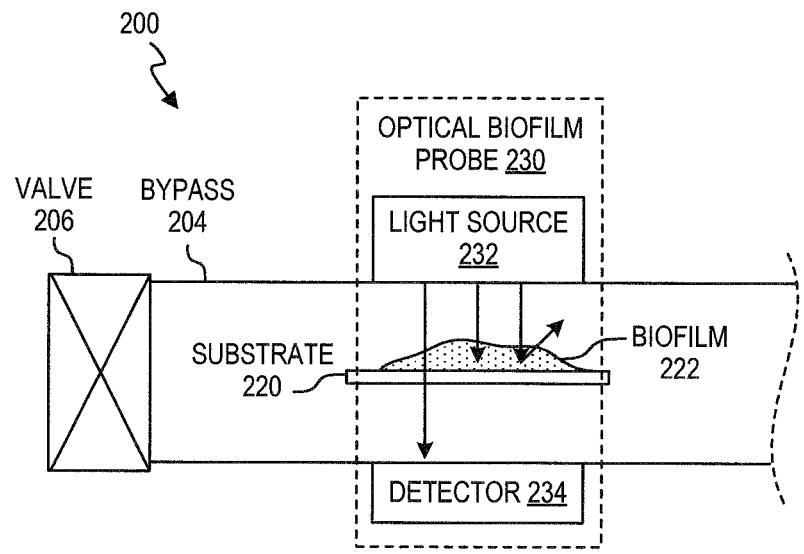
FIG. 2 depicts a diagram of an example optical biofilm probe that performs a transmittance measurement.

FIG. 2 depicts a diagram of an example optical biofilm probe 230 that performs a transmittance measurement and that may serve as or form part of the optical biofilm probe 130. The optical biofilm probe 230 may be at a bypass 204 that is isolated by a valve 206 from fluid flow of a fluid system. A substrate 220 may be disposed within the bypass 204. The bypass 204, the valve 206, the substrate 220, and the optical biofilm probe 230 may together form an apparatus 200 and may be analogous in many respects to the bypass 104, the valve 106, the substrate 120, and the optical biofilm probe 130, respectively.

The optical biofilm probe 230 may include a light source 232 and a detector 234 that are analogous in many respects to the light source 132 and the detector 134, respectively. In particular, the light source 232 and the detector 234 are disposed on different sides of the bypass 204 (i.e., opposite sides), and the substrate 220 is between the light source 232 and the detector 234 for a transmittance measurement by the optical biofilm probe 230.

In some implementations, the bypass 204 may include optically transparent or translucent windows adjacent the light source 232 and the detector 234, such that light emitted by the light source 232 passes into the interior of the bypass 204, interacts with the substrate 220 and any biofilm 222 formed thereon, and passes out of the bypass 204 to the detector 234. The substrate 220 may be non-opaque, and more particularly, may be formed from an optically transparent or translucent material (e.g., glass, polystyrene, another polymeric material, etc.).

When the substrate 220 is clean (i.e., no biofilm formed thereon), light projected by the light source 232 may pass through the substrate 220 and be detected by the detector 234 at a baseline level of intensity. If a biofilm 222 forms on the substrate 220 due to contamination in the fluid system for example, light projected by the light source 232 toward the substrate 220 may be attenuated before detection by the detector 234. For example, attenuation may result from absorption, scattering, or reflection of light by the biofilm 222, and some examples are illustrated as arrows in FIG. 2. Accordingly, a transmittance measurement by the optical biofilm probe 230 compared to the baseline level measurement may be indicative of biofilm incipience (i.e., a first detection of a biofilm) and/or growth and formation of the biofilm 222. Although a biofilm 222 is shown on one side of the substrate 220, biofilm 222 may be permitted to form on two or both sides of the substrate 220 in some implementations, or the substrate 220 may have a different shape altogether.

Figure 3:
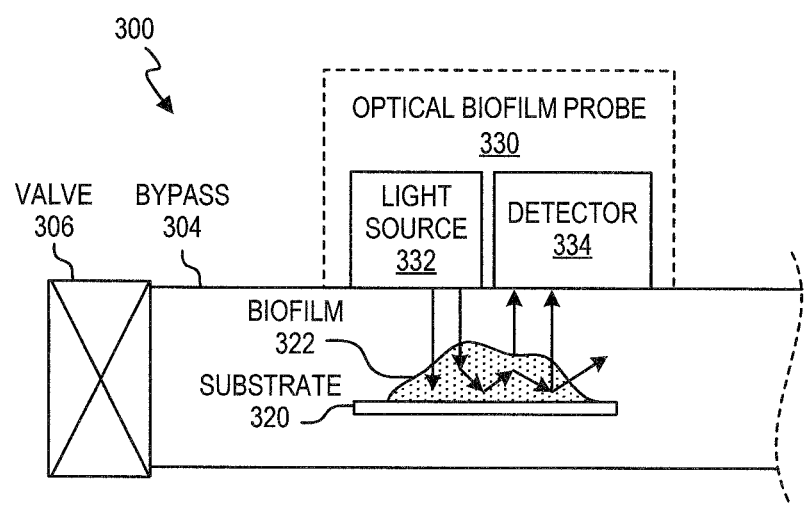
FIG. 3 depicts a diagram of an example optical biofilm probe that performs a reflectance measurement.

FIG. 3 depicts a diagram of an example optical biofilm probe 330 that performs a reflectance measurement and that may serve as or form part of the optical biofilm probe 130. The optical biofilm probe 330 may be at bypass 304 that is isolated by a valve 306 from fluid flow of a fluid system. A substrate 320 may be disposed within the bypass 304. The bypass 304, the valve 306, the substrate 320, and the optical biofilm probe 330 may together form an apparatus 300 and may be analogous in many respects to the bypass 104, the valve 106, the substrate 120, and the optical biofilm probe 130, respectively.

The optical biofilm probe 330 may include a light source 332 and a detector 334 that are analogous in many respects to the light source 132 and the detector 134, respectively. In particular, the light source 332 and the detector 334 are disposed on a same side of the bypass 304 relative to the substrate 320, for a reflectance measurement by the optical biofilm probe 330. As with the bypass 204, the bypass 304 may include optically transparent or translucent windows to allow light emitted by the light source 332 to pass into the bypass 304 and out to the detector 334.

The light source 332 and the detector 334 may be arranged in various configurations to achieve a reflectance measurement. In some implementations, the light source 332 and the detector 334 may be coaxial. In other implementations, the light source 332 and the detector 334 may be adjacent one another and angled such that light emitted from the light source 332 may reflect off of the substrate 320 towards the detector 334. In yet other implementations, the light source 332 and the detector 334 may be coupled into a single optical path into and out of the bypass 304 by a beamsplitter or a bifurcated optical fiber cable.

As with the optical biofilm probe 230, a reflectance measurement by the optical biofilm probe 330 when the substrate 320 is clean may yield a baseline level of light intensity measurement. In some implementations, the substrate 320 may be non-transparent, reflective, or opaque, to provide a controlled baseline level measurement. As a biofilm 322 forms, light transmitted by the light source 332 that is reflected towards the detector 334 may be attenuated (i.e., by scattering, absorption, reflection away from the detector 334, etc., and some examples are illustrated as arrows in FIG. 3). Thus, a reflectance measurement by the optical biofilm probe 330 compared to the baseline level measurement, may indicate biofilm incipience and/or further growth and formation of the biofilm 322. In some cases, light may nevertheless be backscattered or reflected from the biofilm 322 to the detector 334.

Figure 4:
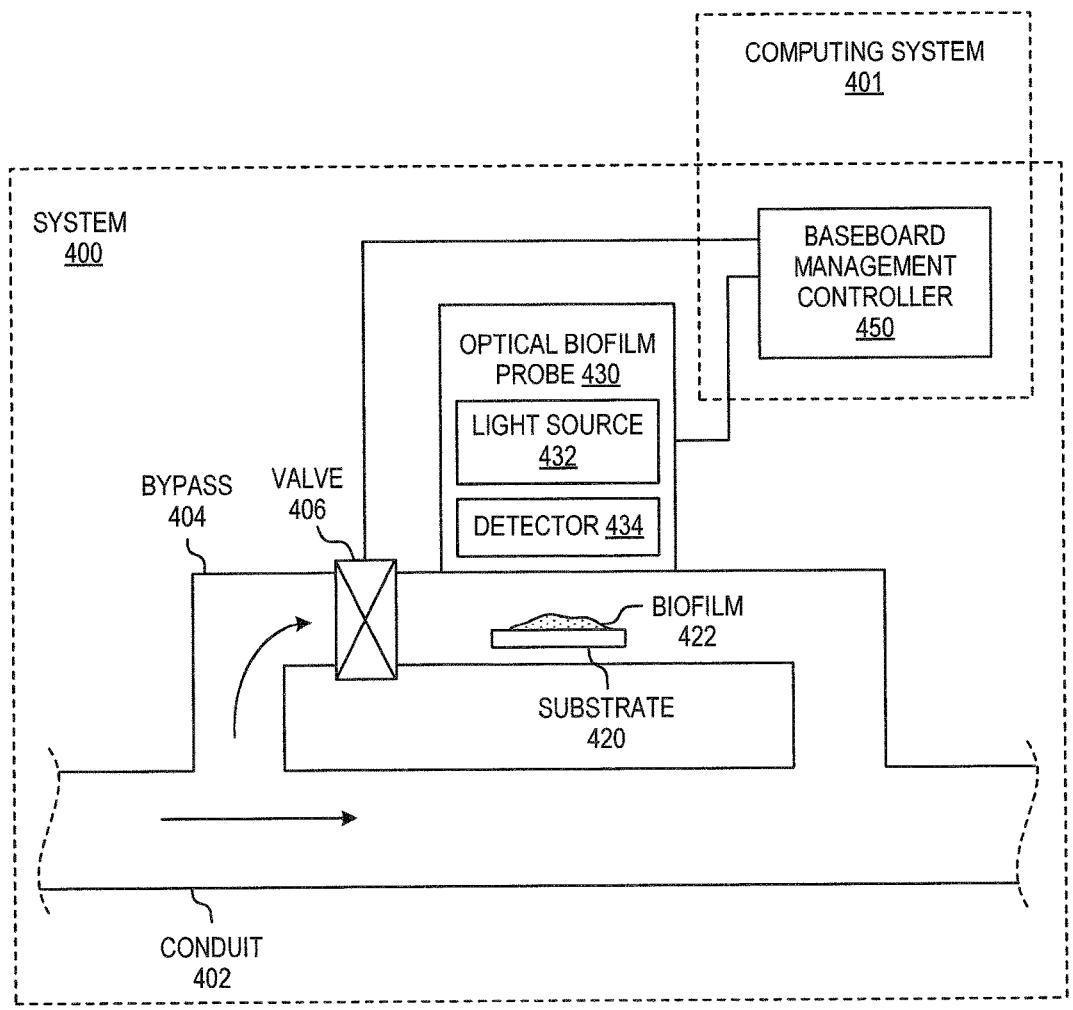
FIG. 4 depicts a diagram of an example apparatus that includes a baseboard management controller to read a signal from an optical biofilm probe.

FIG. 4 depicts a diagram of an example fluid monitoring system 400 that includes a baseboard management controller 450 coupled to an optical biofilm probe 430 at a bypass 404, which may be analogous in many respects to the optical biofilm probe 130 (and more particularly, 230 or 330) and the bypass 104 respectively. For example, the bypass 404 may be connected to a conduit 402 of a fluid system, and a valve 406 may isolate the bypass 404 from flow from the conduit 402. A substrate 420 on which a biofilm 422 may form is disposed within the bypass 404. As with the optical biofilm probes described above (e.g., probes 230, 330), the light source projects light toward the substrate 420, and the detector detects light from the substrate 420 and outputs a signal according to the detected light (i.e., a signal proportional to detected light intensity). Formation of a biofilm 422 on the substrate 420 may affect properties of the detected light (e.g., intensity may be attenuated with greater biofilm 422 formation) and thus the outputted signal.

The fluid system of which the conduit 402 forms a part may be a liquid-cooling system of a computing system 401 (e.g., a server, a high performance computing system, a storage system, etc.), and the baseboard management controller 450 may be a component of that computing system 401. In some implementations, at least some aspects of the system 400, such as the bypass 404 and the optical biofilm probe 430, may be housed within the computing system 401.

The baseboard management controller 450 (which may also be referred to as a lights out management controller, remote management controller, or the like) may be a hardware device (e.g., electronic circuitry or logic) or any combination of hardware and programming to implement the functionality described herein. For example, programming may include executable instructions stored on a non-transitory machine readable medium, such as random access memory (RAM), read-only memory (ROM), electrically erasable programmable read-only memory (EEPROM), flash memory, a hard disk drive, etc., and hardware may include a processing resource, such as a microcontroller, a microprocessor, central processing unit (CPU) core(s), application-specific integrated circuit (ASIC), a field programmable gate array (FPGA), and/or other hardware device suitable for retrieval and/or execution of instructions from the machine readable medium.

The baseboard management controller 450 may communicate with another computing device (not shown) separate from computing system 401 via an out-of-band communication path. A user of the another computing device can interface with the baseboard management controller 450 via the out-of-band communication path to remotely manage aspects of the computing system 401, such as firmware or hardware settings, remote rebooting, remote installation, system diagnostics, and logging. By virtue of interfacing via the out-of-band communication path and the baseboard management controller 450, the user at the another computing device may manage the computing system 401 during normal operation of the computing system 401, in the event of a failure of the computing system 401, or even when the computing system 401 has been powered off and is not running.

In the system 400, the baseboard management controller 450 may actuate the valve 406 to an opened or a closed position. For example, the valve 406 may include a solenoid, a motor, or other actuator that responds to a signal from the baseboard management controller 450 and opens or closes the valve 406 according to the signal.

The baseboard management controller 450 also may read the output signal from the detector 434 of the optical biofilm probe 430. In some implementations, the baseboard management controller 450 may send a signal or command to cause the optical biofilm probe 430 to emit light from the light source 432 and detect light at the detector 434. The baseboard management controller 450 may determine whether the output signal from the detector 434 indicates a presence of biofilm 422 on the substrate 420, as will be described below.

Figure 5:
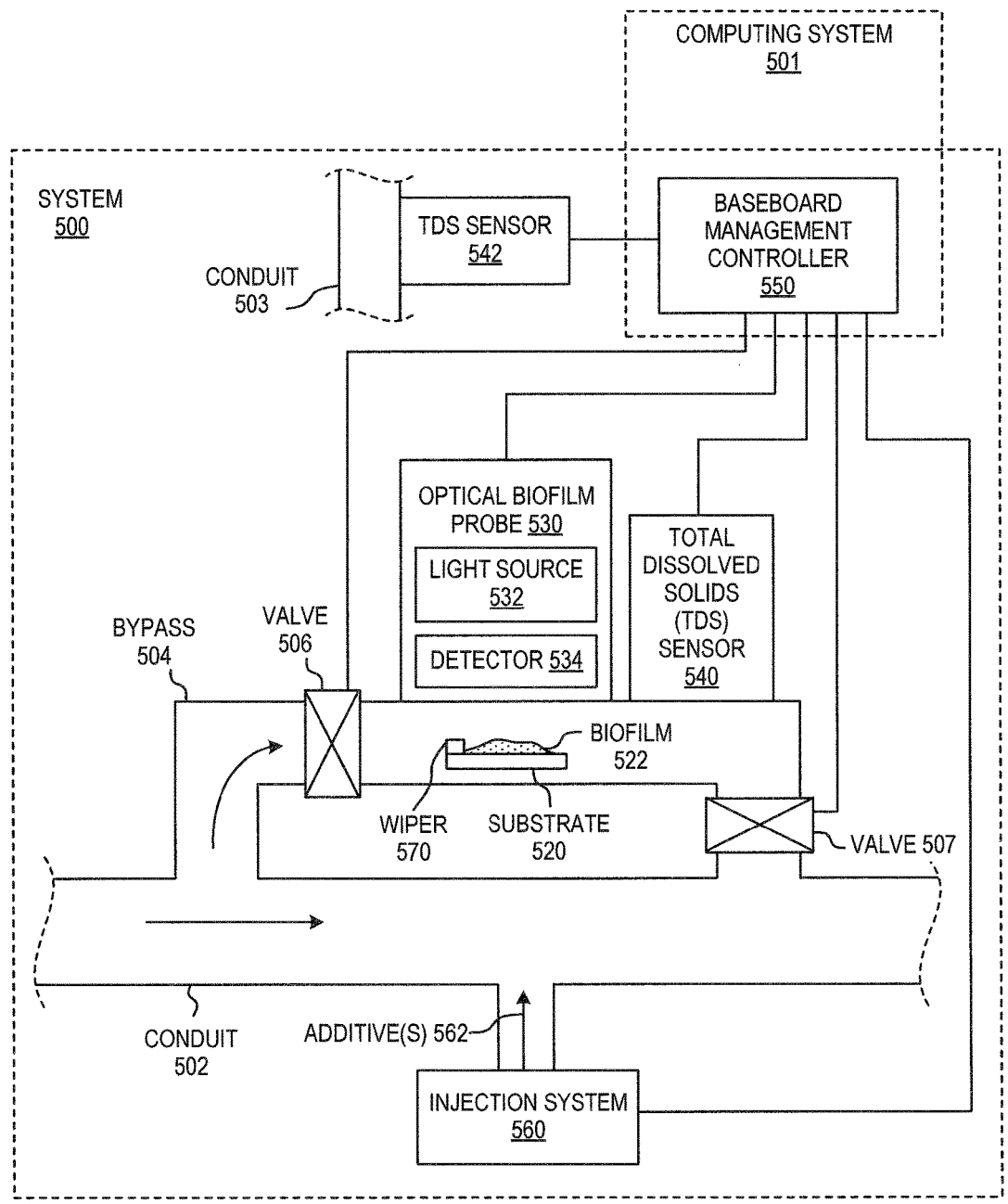
FIG. 5 depicts a diagram of an example system that includes an optical biofilm probe at a bypass and a baseboard management controller to read a signal from the optical biofilm probe.

FIG. 5 depicts a diagram of an example fluid monitoring system 500 for a fluid system. The fluid system may be a liquid-cooling system of a computing system 501. In some implementations, at least some aspects of the system 500 are housed together with the computing system 501.

The system 500 includes a conduit 502 of the fluid system, a bypass 504, a valve 506, a substrate 520, an optical biofilm probe 530, and a baseboard management controller 550, which may be analogous in many respects to, for example, the bypass 104, the valve 106, the substrate 120, the optical biofilm probe 130 (or more particularly, 230 or 330), and the baseboard management controller 450, respectively.

Additionally or alternatively to the valve 506, a valve 507 may be provided on the bypass 504 downstream of the substrate 520. Closing the valve 507, and closing the valve 506 as the case may be, may isolate the bypass 504 and render fluid in the bypass 504 substantially quiescent.

The substrate 520 may allow for a biofilm 522 to develop over time, if there is microbial contamination in the fluid system. As with the optical biofilm probes described above, a light source 532 of the probe 530 projects light toward the substrate 520, and a detector 534 of the probe 530 detects light from the substrate 520 and outputs a signal according to the detected light. The optical biofilm probe 530 may include a light source 532 and a detector 534, and may be arranged in a transmittance mode (e.g., similar to probe 230) or a reflectance mode (e.g., similar to probe 330).

In some implementations, a wiper 570 may be provided within the bypass 504 at the substrate 520 to clean the substrate 520 of any biofilm 522 or other accumulated contamination. A clean substrate 520 may be useful for obtaining a baseline measurement with the optical biofilm probe 530. For example, the wiper 570 may be on the substrate 520 and inside the bypass 504, but actuated to perform a wiping motion on the substrate 520 from outside the bypass 504 by way of a mechanical linkage or magnetic coupling through the bypass 504. Additionally or alternatively, the bypass 504 may include an access port for removal of a dirty substrate and installation of a clean substrate. In some implementations, the light source 532 (or another light source not shown) may emit germicidal ultraviolet light in addition to or as an alternative to wiping the substrate 520 with the wiper 570.

The system 500 also may include a total dissolved solids (TDS) sensor to measure electrical conductivity of fluid in the fluid system, which is indicative of an aspect of fluid quality. In some implementations, the TDS sensor may be located at the bypass 504 (i.e., TDS sensor 540 as illustrated in FIG. 5). Alternatively, the TDS sensor may be located on a conduit of the fluid system, such as the conduit 502 or a conduit 503 (as illustrated in FIG. 5 with TDS sensor 542). In some implementations, multiple TDS sensors may be employed at different points of the fluid system to provide multiple points of fluid quality data. For example, the system 500 may include a TDS sensor 540 at the bypass 504 and a TDS sensor 542 on the conduit 502 or 503.

A TDS sensor may include electrodes connected to a potentiostat. The electrodes extend into the conduit 502 or 503 or bypass 504 and are exposed to the fluid of the fluid system. In some implementations, the potentiostat drives a current (e.g., alternating current) across the electrodes and measures the electrical potential response, which can be converted to an electrical conductivity measurement via Ohm's law, a calibration, or other conversion technique. The electrical conductivity measurement may be further converted to a level of total dissolved solids in the fluid (referred to herein as TDS level). For example, detectable total dissolved solids may include dissolved or mobile ionized particles (e.g., minerals, salts, etc.). The TDS level may be deemed a type of fluid quality measurement. The TDS level (or electrical conductivity measurement) may be analyzed in conjunction with biofilm formation detection from the optical biofilm probe 530, as will be described below.

In some implementations, a TDS sensor may be configured to generate a spectroscopic measurement of the fluid, by measuring an electrical response at different frequencies and monitoring the complex impedance based on phase measurements between current and voltage waveforms. A spectroscopic measurement may be useful for determining the concentration of various chemical components in the fluid.

The baseboard management controller 550 provides manageability functions for the computing system 501. As with the baseboard management controller 450, the baseboard management controller 550 also may actuate the valve 506 (and/or the valve 507) to an opened or closed position, may read a detector signal from the optical biofilm probe 530, and may determine whether the detector signal indicates a presence of biofilm 522 on the substrate 520. The baseboard management controller 550 also may read the electrical conductivity measurement (or the TDS level) from the TDS sensor 540 or 542.

The baseboard management controller 550 may generate an overall fluid quality measurement for the fluid system based on the electrical conductivity measurement (or the TDS level) and the detector signal of the optical biofilm probe 530. For example, the baseboard management controller 550 may mathematically combine the electrical conductivity measurement (or the TDS level) and the detector signal by algebraic operations, logical operations, or other operations to generate the overall fluid quality measurement.

In some implementations, the baseboard management controller 550 may periodically read the detector signal from the optical biofilm probe 530 and/or a TDS sensor measurement (i.e., conductance or TDS level), for example, at a sampling rate on the order of hours or days, or may request or command a measurement from the probe 530 or TDS sensor 540 or 542. The baseboard management controller 550 may store a plurality of detector signals or TDS sensor measurements sampled over time, or may transmit detector signals or TDS sensor measurements to the computing system 501 or another computing device (e.g., to a remote terminal via an out-of-band communication path).

In some implementations, the baseboard management controller 550 may compare the detector signal from the optical biofilm probe 530 and/or the TDS sensor measurement to a respective baseline level measurement obtained with the fluid system or the substrate 520 in a known state (e.g., a clean or uncontaminated state), and may monitor for signal changes, such as changes greater than a predetermined threshold. Changes greater than a predetermined threshold may indicate the presence or formation of biofilm 522 or contamination or impurities in the fluid system.

In some implementations, the baseboard management controller 550 may provide an alert in response to a determination that the detector signal indicates the presence of biofilm 522 on the substrate 520. For example, the alert (as well as the overall fluid quality measurement, the TDS sensor measurement, and/or the detector signal of the optical biofilm probe) may be provided at an interface of the computing system 501, and additionally or alternatively, via an out-of-band communication path to another computing device.

In some implementations, the system 500 may include an injection system 560. The injection system 560 may include a pump, dispenser, injector, or the like that can deliver various additives 562 to the fluid system. Although the injection system 560 is pictured in FIG. 5 as dispensing into the conduit 502, the injection system 560 may be located instead at other portions of the fluid system such as conduit 503. The additives 562 may be, for example, reverse osmosis water, deionized water, a biocide (e.g., isothiazalone, DBNPA (2,2-dibromo-3-nitrilopropionamide), and/or hydrogen peroxide silver), a corrosion inhibitor (e.g., sodium silicate, sodium hexametaphosphate, and/or a molybdate-based corrosion inhibitor), or other chemistry-altering additives (e.g., chemicals to adjust pH).

The baseboard management controller 550 may, in some implementations, control the injection system 560 to deliver an additive 562 into the fluid system in response to an analysis of the detector signal and/or the TDS sensor measurement. As one illustration, the baseboard management controller may control the injection system 560 to deliver an additive (e.g., biocide) in response to a determination that the detector signal of the probe 530 indicates the presence of biofilm 522 on the substrate 520. In another example, the baseboard management controller may control the injection system 560 to deliver an amount of additive that is a function of a level of the detector signal and/or the TDS sensor measurement (e.g., based on a predetermined relationship stored in a lookup table, a database, a parametric equation, etc.).

In some implementations, a complete flush and subsequent refill of the fluid system may be useful for responding to changes in overall fluid quality or formation of biofilm, and in some instances, may be deemed a more aggressive response or corrective action than delivering additives to the fluid system. For example, in some implementations, the baseboard management controller 550 may determine that an absolute value or relative value (i.e., compared to a baseline level) of the overall fluid quality measurement, the TDS sensor measurement, or the detector signal of the optical biofilm probe 530 meets or exceeds a flush threshold level (which may be the same as or different from the predetermined level described above). In response to such a determination, the baseboard management controller 550 may actuate a flushing mechanism of the fluid system, which may include, for example, opening flush valves to drain the fluid system and then causing a filling system (which may be the injection system 560) to rinse and/or refill the fluid system.

Figure 6:
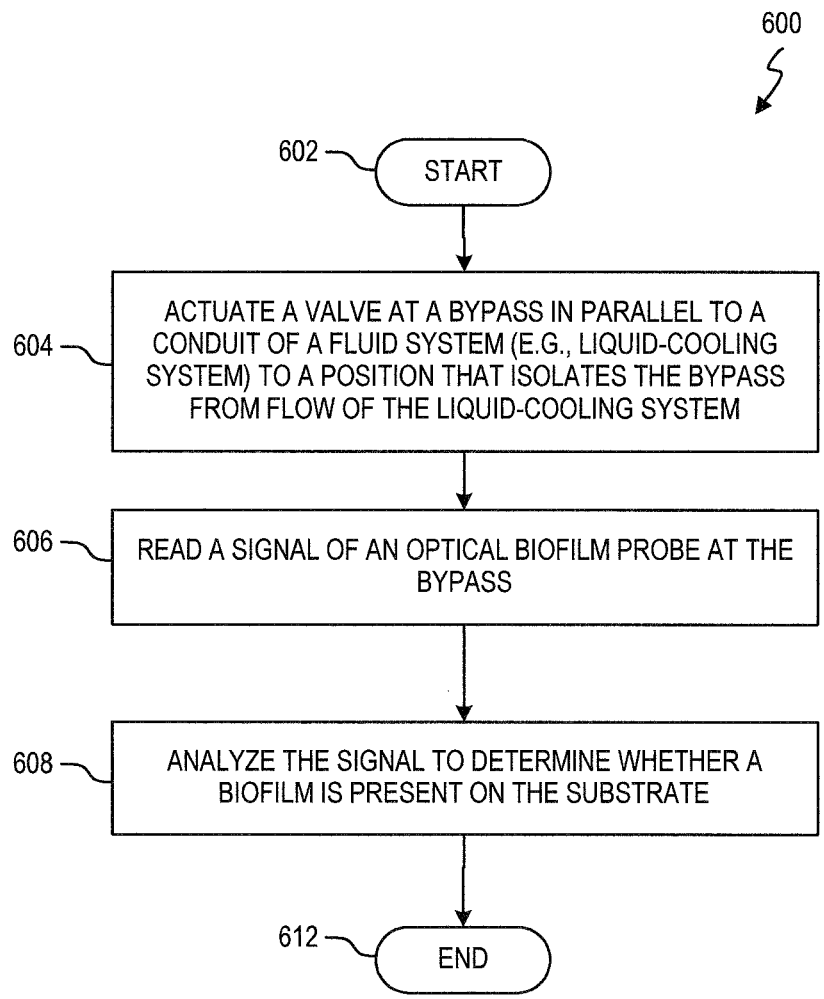
FIG. 6 is a flow diagram depicting an example method to determine whether a biofilm is present on a substrate disposed within a bypass.

FIG. 6 is a flow diagram depicting an example method 600 to determine whether a biofilm is present on a substrate disposed within a bypass. Method 600 may be performed a controller, and more particularly by the baseboard management controller 450 or 550, in a system analogous to the system 400 or 500.

The method 600 begins at block 602 and continues to block 604, where the baseboard management controller actuates a valve at a bypass in parallel to a conduit of a fluid system (such as a liquid-cooling system) to a position that isolates the bypass from flow of the fluid system. At block 606, the baseboard management controller reads a signal of an optical biofilm probe (e.g., 430 or 530) at the bypass. At block 608, the baseboard management controller may analyze the signal to determine whether a biofilm is present on the substrate. At block 612, the method 600 ends.

Figure 7:
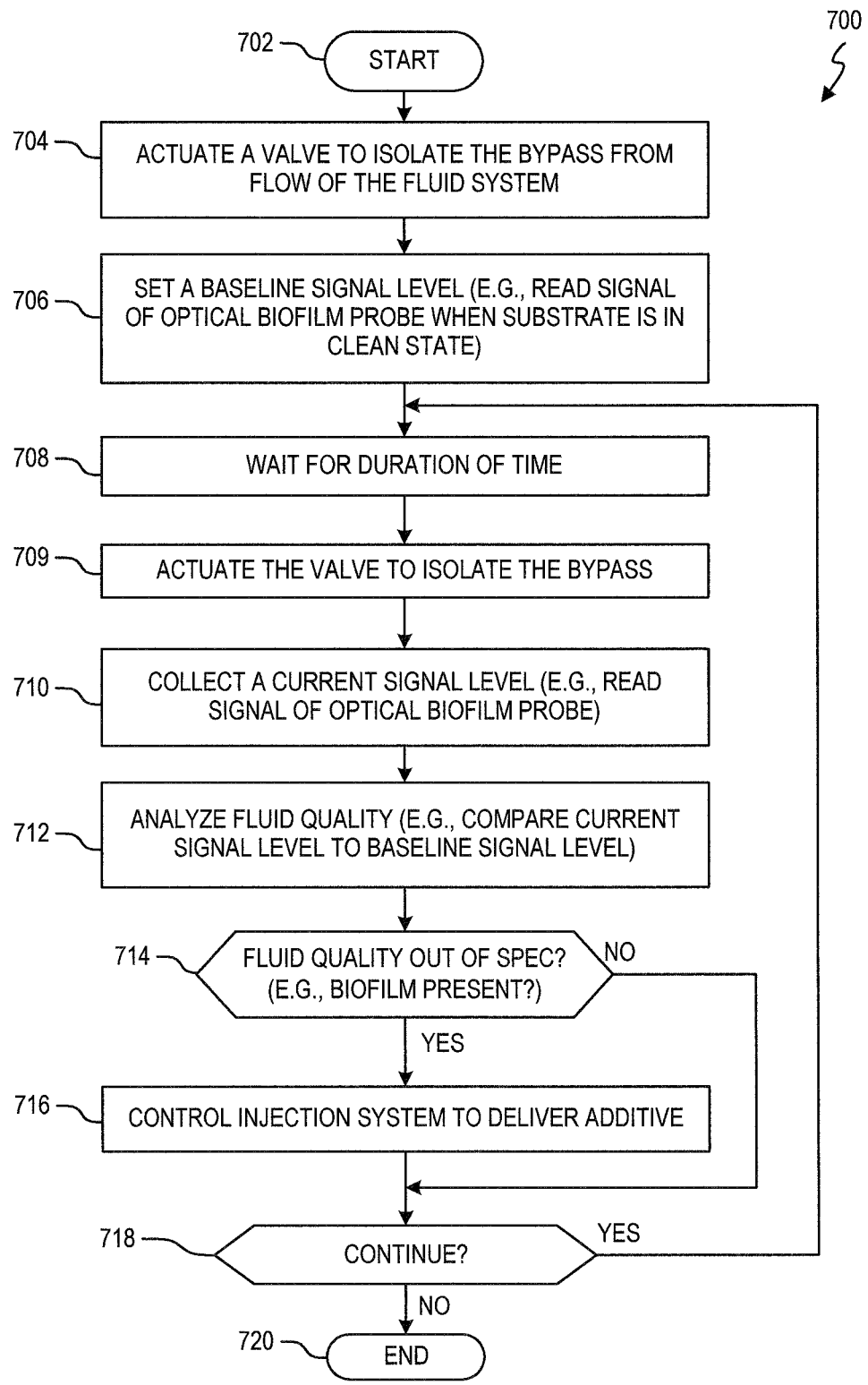
FIG. 7 is a flow diagram depicting an example method to analyze fluid quality in a liquid-cooling system.

FIG. 7 is a flow diagram depicting an example method 700 to analyze fluid quality in a fluid system, such as a liquid-cooling system for a computer. Method 700 may be performed by a controller, such as the baseboard management controller 550, in a system analogous to system 500. For example, the baseboard management controller (550) may be in communication with an optical biofilm probe similar to the probe 530, and the baseboard management controller (550) may be further in communication with a TDS sensor similar to the TDS sensor 540 or 542.

The method 700 begins at 702 and continues to block 704, where the baseboard management controller actuates a valve at a bypass in parallel to a conduit of the fluid system (e.g., a liquid-cooling system) to a position that isolates the bypass from flow of the rest of the fluid system. The baseboard management controller may wait a predefined settling period before proceeding, to allow fluid in the bypass to become quiescent.

At block 706, the baseboard management controller sets a baseline optical signal level by reading a detector signal from the optical biofilm probe when a substrate in the bypass is in a clean state. For example, the substrate may be clean by virtue of a wiper previously wiping the substrate or by virtue of the substrate being recently installed. In some implementations, the baseboard management controller may also read a TDS sensor measurement (e.g., electrical conductivity or TDS level) at block 706 to set a baseline TDS signal level. After setting the baseline signal level(s), the baseboard management controller may actuate the valve to restore flow to the bypass.

At block 708, the baseboard management controller waits a duration of time. For example, the duration may be a preprogrammed (e.g., user-defined) periodic interval, such as an interval on the order of hours to days. Alternatively, the duration of time may be indefinite until an event trigger, such as a user command or scripted command.

At block 709, the baseboard management controller may actuate the valve to isolate the bypass from flow of the fluid system and may wait the predefined settling period. Block 709 may be similar to block 704.

At block 710, the baseboard management controller collects current signal level(s). For example, the baseboard management controller may read a detector signal of the optical biofilm probe and/or read a TDS sensor measurement from the TDS sensor. After collecting the current signal level(s), the baseboard management controller may actuate the valve again to restore flow to the bypass.

At block 712, the baseboard management controller analyzes the current signal level(s) to assess fluid quality in the fluid system. For example, analysis may include comparing the current signal level collected at block 710 to the baseline signal level set at block 706, for each of the optical biofilm probe detector signal and the TDS sensor measurement respectively. As discussed above, a decrease in the current optical biofilm probe signal level in comparison to the baseline optical signal level, may indicate that a biofilm is present and/or forming on the substrate. A change in TDS sensor measurement may indicate a shift in the chemistry of the fluid.

In some implementations, the baseboard management controller may maintain a specification of tolerable ranges of changes in optical biofilm probe signal levels and/or TDS sensor signal levels. The ranges may be predetermined based on known accuracy and precision characteristics of the probe and sensor, for example. In some implementations, the baseboard management controller may, at block 712, issue an alert in response to a determination that one or more of the current signal levels diverge from the baseline signal level.

If the analysis at block 712 indicates that one or more of the fluid quality signal levels is outside of the specification, method 700 may proceed to block 716. Otherwise, method 700 may proceed to block 718. Block 716 will first be described.

At block 716, the baseboard management controller may control an injection system to deliver an additive to the fluid system. For example, the baseboard management controller may analyze the fluid quality signals to determine (at either block 712 or block 716) what type of additive to deliver. In some instances, if the current optical biofilm probe signal levels indicate the presence of a biofilm and the TDS sensor signal levels are within specification, the baseboard management controller may select a biocide as the additive. In other instances, if the current optical biofilm probe signal levels indicate the presence of a biofilm and TDS sensor signal levels indicate a shift in fluid chemistry, the baseboard management controller may select appropriate chemical additives (e.g., acids, bases, buffers, etc.) to rebalance the fluid chemistry in addition to or as an alternative to delivering a biocide. In yet other instances, if no biofilm is detected and TDS sensor signal levels indicate a shift in fluid chemistry, the baseboard management controller may select appropriate chemical additives to rebalance the fluid chemistry without also selecting a biocide additive.

At block 718, the baseboard management controller determines whether to continue fluid monitoring. For example, the baseboard management controller may be instructed to stop by a user or other automated commands. If fluid monitoring is to continue, method 700 proceeds back to block 708. Otherwise, method 700 ends at block 720.

In view of the foregoing description, it can be appreciated that an optical biofilm probe installed at a fluid system, such as a liquid-cooling system or a manufacturing fluid delivery system, may provide fast and efficient real time detection of biofilm formation, particularly in comparison to manual fluid sampling and lab analysis. Such real time detection by the optical biofilm probe may enable timely (e.g., early) intervention including fluid chemistry adjustments or biocide delivery, carried out either manually or automatically. Additionally, costly decontamination or part replacement procedures may be avoided owing to timely intervention. Moreover, a corroborative and holistic view of fluid quality may be provided, by virtue of employing an optical biofilm probe and a TDS sensor together.

In the foregoing description, numerous details are set forth to provide an understanding of the subject matter disclosed herein. However, implementation may be practiced without some or all of these details. Other implementations may include modifications and variations from the details discussed above. It is intended that the following claims cover such modifications and variations.

What is claimed:

1. A system comprising:
   a bypass connected in parallel to a conduit of a liquid-cooling system of a computer;
   a valve that, in a closed position, isolates the bypass from flow of the liquid-cooling system;
   a substrate disposed within the bypass and in contact with fluid of the liquid-cooling system in the bypass;
   an optical biofilm probe at the bypass to detect biofilm formation on the substrate, the optical biofilm probe including:

a light source to project light into the bypass and towards the substrate, and a detector to detect light from the substrate and output a signal according to detected light, wherein biofilm formation on the substrate affects properties of the detected light; and a baseboard management controller of the computer to:

actuate the valve to the closed position, read the signal from the optical biofilm probe when the valve is in the closed position, and determine whether the signal indicates a presence of biofilm on the substrate.

2. The system of claim 1, wherein the baseboard management controller is to provide an alert in response to a determination that the signal indicates the presence of biofilm on the substrate.

3. The system of claim 1, further comprising a total dissolved solids sensor disposed at the bypass to measure electrical conductivity of fluid in the bypass, wherein the baseboard management controller is to generate an overall fluid quality measurement of the liquid-cooling system based on the electrical conductivity and the signal of the detector of the optical biofilm probe.

4. The system of claim 1, further comprising an injection system coupled to the liquid-cooling system, wherein the baseboard management controller is to control the injection system to deliver an additive into the liquid-cooling system in response to a determination that the signal indicates the presence of biofilm on the substrate.

5. The system of claim 1, wherein the baseboard management controller is to read the signal periodically.

6. The system of claim 1, wherein the light source and the detector are disposed on different sides of the bypass, the substrate is between the light source and the detector for a transmittance measurement by the optical biofilm probe, and the substrate is non-opaque.

7. The system of claim 1, wherein the light source and the detector are disposed on a same side of the bypass relative to the substrate for a reflectance measurement by the optical biofilm probe.

8. The system of claim 1, wherein the substrate comprises a material noninhibitive of biofilm formation.

9. The system of claim 1, further comprising a wiper disposed within the bypass to clean the substrate.

* * * * *